(12) United States Patent
Allison et al.

(10) Patent No.: US 7,344,888 B2
(45) Date of Patent: Mar. 18, 2008

(54) BLUEBERRY RED RINGSPOT VIRUS, SEQUENCES, PROMOTERS, AND USES THEREOF

(75) Inventors: Richard F Allison, Leslie, MI (US); Jerri Gillett, East Lansing, MI (US); Christy Mecey, Leslie, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 507 days.

(21) Appl. No.: 10/793,454

(22) Filed: Mar. 4, 2004

(65) Prior Publication Data

US 2004/0255348 A1    Dec. 16, 2004

Related U.S. Application Data

(63) Continuation of application No. PCT/US02/28260, filed on Sep. 5, 2002.

(60) Provisional application No. 60/318,050, filed on Sep. 7, 2001.

(51) Int. Cl.
*C07H 21/04* (2006.01)
*C12N 15/82* (2006.01)
*C12N 5/04* (2006.01)

(52) U.S. Cl. .................. 435/468; 435/320.1; 435/419; 536/24.1; 800/278

(58) Field of Classification Search ...................... None
See application file for complete search history.

(56) References Cited

U.S. PATENT DOCUMENTS 5,641,876 A    6/1997  McElroy et al. ........... 536/24.1
6,100,450 A *  8/2000  Thomas et al. ............. 800/287

6,255,560 B1    7/2001  Fraley et al. ............... 800/278

OTHER PUBLICATIONS

Odell, J.T., Nagy, F. and Chua, N.H. (1985) Identification of DNA sequences required for the activity of the cauliflower mosaic virus 35S promoter. Nature 313: 810-812.

Benfey, P.N. and Chua, N.H. (1990) The Cauliflower Mosaic Virus 35S promoter: combinatorial regulation of transcription in plants. Science 250: 959-966.

Daubert, S.D., et al., (1984) Expression of Disease Symptoms in Cauliflower Mosaic Virus Genomic Hybrids. Journal of Molecular and Applied Genetics 2: 537-547.

Dixon, L.K., et al., (1983) Mutagenesis of Cauliflower Mosaic Virus. Gene 25: 189-199.

Mesnard, J., et al. (1990) The Cauliflower Mosaic Virus Gene III product is a non-sequence specific DNA binding protein. Virology 174: 622-624.

(Continued)

*Primary Examiner*—Ashwin Mehta
(74) *Attorney, Agent, or Firm*—Harness, Dickey & Pierce, P.L.C.

(57) ABSTRACT

A nucleic acid sequence of the blueberry red ringspot virus is disclosed. Also disclosed are putative promoter regions of the sequence and promoter regions capable of directing transgene expression in plants, including tissue-specific expression. Also disclosed are expression vectors, transformed plant cells and plants containing a blueberry red ringspot virus promoter and an encoded product for expression. Methods for diagnosis of blueberry red ringspot virus infection are also provided.

10 Claims, 2 Drawing Sheets

Figure 1:
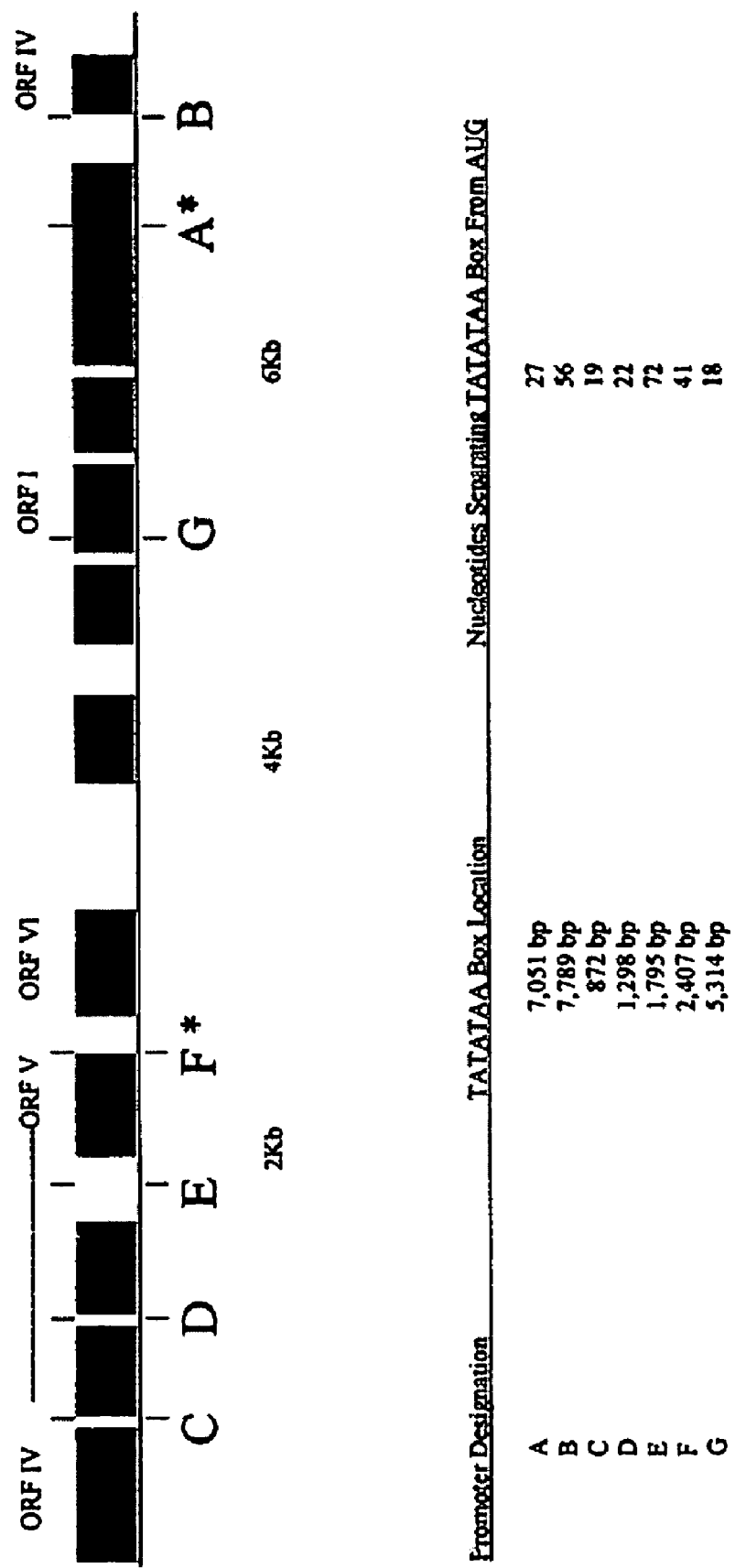

BRRV Genome with Putative Open Reading Frames and Promoter Locations

| Promoter Designation | TATATAA Box Location | Nucleotides Separating TATATAA Box From AUG |
|---|---|---|
| A | 7,051 bp | 27 |
| B | 7,789 bp | 56 |
| C | 872 bp | 19 |
| D | 1,298 bp | 22 |
| E | 1,795 bp | 72 |
| F | 2,407 bp | 41 |
| G | 5,314 bp | 18 |

OTHER PUBLICATIONS

Pfeiffer, P. and Hohn, T. (1983) Involvement of reverse transcription in the replication of cauliflower mosaic virus. Cell 33: 781-789.

Takatsuji, H., et al. (1992) Cauliflower Mosaic Virus reverse transcriptase—activation by proteolytic processing and functional alteration by terminal deletion. Journal of Biological Chemistry 267: 11579-11585.

Thomas, C. L. et al. (1993) A mutation in Cauliflower Mosaic Virus Gene I interferes with virus movement but not with virus replication. Virology 192: 415-421.

Boyer, T.G., and Maquat, L.E. (1990). Minimal sequence and factor requirements for the initiation of transcription from an atypical TATATAA box-containing housekeeping promoter. J. Biol. Chem. 265: 20524-20532.

Chalfie, M., Tu, Y., Euskirchen, G., Ward, W.W., and Prasher, D.C. (1994), Green fluorescent protein as a marker for gene expression. Science 263: 802-805.

Kim, K.S., Ramsdell, D.C., Gillett, J.M., and Fulton, J.P. (1981). Virions and substructural changes associated with blueberry red ringspot disease. Phytopathology 71: 673-678.

Gillett, J. M., and Ramsdell, D. C. (1984). Detecting the Inclusion forming Blueberry Red Ringspot Virus with ELISA. Phytopathology 74: 862.

Hepp, et al. Blueberry Red Ringspot Virus Detection in Crude Sap of Highbush Blueberry Plants. Plant Disease, Jun. 1987, vol. 71, No. 6, pp. 536-538. see whole document.

Maiti, et al. Gene expression regulated by gene VI of caulimovirus: transactivation of downstream genes of transcripts by gene VI of peanut chlorotic streak virus in transgenic tobacco. Virus Research, 1998, vol. 57, pp. 113-124, especially pp. 117-121.

Maiti, et al. Isolation and expression analysis of peanut chlorotic streak caulimovirus (PCISV) full-length transcript (FLt) promoter in transgenic plants. Biochem. Biophys. Res. Comm. 1998, vol. 244, pp. 440-444, especially pp. 441-443.

Glasheen, et al. Cloning, sequencing, and promoter identification of Blueberry red ringspot virus, a member of the family Caulimoviridae with similarities to the "Soybean chlorotic mottle-like" genus. Arch. Virol., 2002, vol. 147, pp. 2169-2186, see whole document.

Doolittle, R.F., Feng, D.F., Johnson, M.S. and McClure, M.A. (1989) Origins and evolutionary relationships of retroviruses. Q. Rev. Biol. 64:1-30.

Ducasse, D.A., Mushegian, A.R. and Shepard, R.J. (1995) Gene I mutants of peanut chlorotic streak virus, a caulimovirus, replicate in plants but do not move from cell to cell, J. Virol., 69:5781-5786.

Hutchinson, M.T. and Varney, E.H. (1954) Ringspot: A virus disesase of cultivated blueberry. Plant Dis. Rep., 38:260-262.

Ramsdell, D.C., Kim, K.S. and Fulton, J.P. (1987) Red ringspot of blueberry, p. 121-126. In: R.H. Converse (ed.) Virus Diseases of Small Fruits. U.S. Dept. of Ag., Agr. Res. Svc., Wash. D.C. Hdbk. 631.

Torruella, M., Gordon, K. and Hohn, T. (1989) Cauliflower mosaic virus produces an aspartic proteinase to cleave its polyproteins. EMBO J. 8:2819-2825.

* cited by examiner

Plurality: 2.00  Threshold: 1  AveWeight 1.00  AveMatch 1.00  AvMisMatch 0.00

Consensus Sequence

Symbol comparison table: pileupdna.cmp  CompCheck: 6876

```
         GapWeight: 5
   GapLengthWeight: 1
```

PileUp   MSF: 206   Type: N   December 6, 2000 12:08  Check: 1484 ..

```
Name: putpromotera  Len: 206  Check: 8733  Weight: 1.00
Name: putpromoterd  Len: 206  Check: 2099  Weight: 1.00
Name: putpromotere  Len: 206  Check: 6882  Weight: 1.00
Name: putpromoterf  Len: 206  Check: 5015  Weight: 1.00
Name: putpromoterg  Len: 206  Check: 6944  Weight: 1.00
Name: putpromoterb  Len: 206  Check: 8395  Weight: 1.00
Name: putpromoterc  Len: 206  Check: 3416  Weight: 1.00
```

```
                1                                                           50
putpromotera  --------  ----------  ----------  ----------  ----------
putpromoterd  ----------  ----------  ----------  ----------  -------ata
putpromotere  acgatgcgaa  gatgaaggaa  tcatcttatc  acagccaaaa  gcaaaaatag
putpromoterf  ----------  ----------  ----------  ----------  ---------a
putpromoterg  ----------  ----------  ----------  ----------  ----------
putpromoterb  ----------  ----------  ----------  ----------  ---------g
putpromoterc  ----------  ----------  ----------  ----------  ---------a
   Consensus  ----------  ----------  ----------  ----------  ---------A 51                                                          100
putpromotera  -acactatcc  gagggaatgc  ccaacctaca  aaagaatga   tcatcgataa
putpromoterd  gaaaaagtcc  acatagtgcg  ccagcattct  atgtagaaaa  tcattcagaa
putpromotere  cacataaaga  aattgatttc  tttggattca  tatttcagaa  ggagaaataa
putpromoterf  tttactatca  aaacctttta  ttttaaaaac  agattcaaaa  tatgttacag
putpromoterg  ------atag  aataatttct  aaaaataaga  aagaacaagt  tctaggaata
putpromoterb  gtccagtaac  aggacgatta  gaagatggaa  tattaaatct  agattgttta
putpromoterc  taaagtagcc  cttatgatta  caatattaat  agaaaaaagg  aaattccttg
   Consensus  -ACA-TATCC  AATA-GTTTA  CAAGA-TA-A  AAATA-AA-A  TCATTGATAA 101                                                          150
putpromotera  tcaaccagaa  ccatgttatc  aaaaagattc  acctttccca  catctatatc
putpromoterd  ataaaaagag  cattaagaag  aattgttata  aattataaag  ctattgaatg
putpromotere  tactacaacc  acatattttt  ggaaaaatta  gtattattcc  ctgatgaatt
putpromoterf  gattttttgag  atataaaata  aaagccaatt  ataatcaagg  acggttgact
putpromoterg  attaaaggaa  atctgaaata  tggagtatta  agttcgacgt  cgtctacact
putpromoterb  actaatggag  aagaattatt  aaaacaatgg  acagcaaaac  aatcattatc
putpromoterc  tacccactat  atatcaattt  gattcaggag  taccaatgat  tataggaaat
   Consensus  -ATAAAAGAG  ATATAA-ATT  AAAACAATTA  A-ATTAAAA-  CAT-TGAATT 151                                                          200
putpromotera  atacctttga  tccacaatta  aataatataa  cagatatgct  tatgtatata
putpromoterd  aagccaccat  tggaacaccl  aaacattacc  cagagcagat  tatataa---
putpromotere  cagaatcgaa  agcaattaca  aagatttctt  ggaaatttaa  attatataa-
putpromoterf  agatggcaac  ttgaattatc  acaattcaac  tatagaactt  tttatataa-
putpromoterg  tcgccatacc  attagtaact  aagaatttaa  gccaatctat  aggaatatta
putpromoterb  aacacaaatt  gatgctacca  tccgagacat  ggatgctgag  aatatataa-
putpromoterc  aacttttaa   gattatatta  cccattttgt  caatatctat  cttatataa-
   Consensus  AAGCC--AAA  T-TAATAACA  AA-AATTTAT  -AAA-TT-AT  --TATATAAA 201
putpromotera  a-----
putpromoterd  ------
putpromotere  ------
putpromoterf  ------
putpromoterg  tataaa
putpromoterb  ------
```

FIGURE 2

BLUEBERRY RED RINGSPOT VIRUS, SEQUENCES, PROMOTERS, AND USES THEREOF

CROSS REFERENCE TO RELATED APPLICATIONS

This application is a continuation of PCT/US02/28260, filed Sep. 5, 2002, which claims priority to U.S. Provisional Ser. No. 60/318,050, filed Sep. 7, 2001, both of which are incorporated by reference herein.

BACKGROUND OF THE INVENTION (1) Field of the Invention

This invention relates to nucleic acid sequences of the blueberry red ringspot virus and, more particularly, to the nucleic acid sequence of the virus, the identification of promoters, and the use of the promoters in the expression of recombinant genes in transgenic plants, including tissue-specific expression in plants. The invention also relates to sequences of the blueberry red ringspot virus useful in the diagnosis of disease in plants, and related methods thereof.

(2) Description of the Related Art

Recombinant viral promoters can be used to direct the expression of operably linked heterologous genes. Such expression can occur in a transgenic environment. For expression of transgenes in plants, a promoter from Cauliflower Mosaic Virus (CaMV) is widely used, for example as disclosed in U.S. Pat. No. 6,255,560 to Fraley et al. Expression of transgenes in plants under the control of a CaMV promoter tends to be at high levels and show little tissue- or cell-type specificity. This virus is unusual, in that it appears to comprise only two promoters. One promoter appears to control the transcription of the entire viral genome into an RNA copy. This promoter (the "35S" promoter) is a tandem repeat of an approximately 350 base pair sequence. Within this sequence are domains involved with tissue specific expression of genes expressed from the promoter (Odell, J. T., Nagy, F. and Chua, N. H. (1985) Identification of DNA sequences required for the activity of the cauliflower mosaic virus 35S promoter. *Nature* 313: 810-812; Benfey, P. N. and Chua, N. H. (1990) The Cauliflower Mosaic Virus 35S promoter: combinatorial regulation of transcription in plants. *Science* 250: 959-966; Daubert, S. D., et al., (1984) Expression of Disease Symptoms in CaMV Genomic Hybrids. *Journal of Molecular and Applied Genetics* 202: 1043-1045; Dixon, L. K., et al., (1983) Mutagenesis of Cauliflower Mosaic Virus. *Gene* 25: 189-199; Mesnard, J., et al. (1990) The Cauliflower Mosaic Virus Gene III product is a non-sequence specific DNA binding protein. *Virology* 174: 622-624; Pfeiffer, P. and Hohn, T. (1983) Involvement of reverse transcriptase in the replication of cauliflower mosaic virus. *Cell* 33: 781-789; Takatsuji, H., et al. (1992) Cauliflower Mosaic Virus reverse transcriptase—activation by proteolytic processing and functional alteration by terminal deletion. *Journal of Biological Chemistry* 267: 11579-11585; Thomas, C. L. et al. (1992) A mutation in Cauliflower Mosaic Virus Gene I interferes with virus movement but not with virus replication. *Virology* 74: 1141-1148). This promoter has proven useful for directing the expression of heterologous genes in transgenic plants.

Because transgenes under CaMV promoter control may not be suitable for all uses, there is a need for the identification and characterization of more plant virus promoters. For example, there is the need for tissue specific promoters that can direct expression of an operably linked gene to a subset of tissues within a transgenic plant. Furthermore, there is a need for a strategy for identifying putative promoters, and a further need to demonstrate the operability of a putative promoter in a transgenic environment.

The blueberry red ringspot virus is a virus with a limited host range: it is believed to infect only blueberry plants. Disease symptoms are observed primarily in the months of July, August and September, and comprise red spots primarily on upper leaf surfaces (Hutchinson, M. T. (1950) Can you recognize the symptoms of stunt disease? Proceedings 19$^{th}$ Annual Blueberry Open House 19: 9-11; Ramsdell, D. C., Kim, K. S. and Fulton, J. P. (1987) Red Ringspot of Blueberry. In: Converse, R. H. (ed.) *Virus Diseases of Small Fruits*. U.S. Department of Agriculture, Agr. Res. Svc., Washington, DC Handbook 631; Kim, K. S., Ramsdell, D. C., Gillett, J. M. and Fulton, J. P. (1981) Virions and substructural changes associated with blueberry red ringspot disease. Phytopathology 71: 673-678; Gillett, J. M. (1988) Physical and Chemical properties of Blueberry Red Ringspot Virus. Master's thesis, Michigan State University; Hutchinson, M. T. and Varney, E. H. (1954) Ringspot: A virus disease of cultivated blueberry. *Plant Disease Reports* 38: 260-262). A sequence of a putative blueberry red ringspot virus has been published on the http World Wide Web at ncbi.nlm.nih.gov with accession numbers NC 003138 and AF404509. This sequence has a length of 8,303 base pairs. No promoters are disclosed or identified in these sequence listings. Furthermore, this sequence has several differences with the sequence of the virus of the present invention as disclosed herein.

BRIEF DESCRIPTION OF THE INVENTION

The present invention involves the discovery and characterization of the nucleic acid sequence of the genome of blueberry red ringspot virus (BRRV). The genome comprises a circular, double-stranded DNA molecule. The molecule has a length of at least 8,241 base pairs. Promoters are identified in the sequence based upon analysis of sequence structure. Recombinant promoters derived from BRRV DNA are used to direct gene expression.

In some embodiments, the present invention is directed to a fragment of the viral nucleic acid which putatively functions as a promoter in plant cells. Each of these putative promoter regions comprises a "TATATAA box" or a "TATA box" and a nearby open reading frame located 3' to the TATATAA box or TATA box. In another embodiment, a consensus sequence for the blueberry red ringspot putative promoters is provided. Also within the scope of the invention are methods for identifying putative promoter sequences of the Blueberry Red Ringspot Virus.

In preferred embodiments, the invention is drawn to a recombinant nucleic acid comprising a fragment of the full-length nucleic acid of the BRRV which functions as a promoter (a "BRRV promoter"). In a preferred embodiment, the present invention provides a recombinant nucleic acid comprising a BRRV promoter operably linked to a gene for expression as a transgene in a host organism or cell. The transgene preferably encodes a polypeptide or a regulatory RNA molecule. Preferably, the host organism is a plant, and the host cell is a plant cell. In another preferred embodiment, a recombinant nucleic acid comprising a BRRV promoter operably linked to a gene for expression as a transgene, provides tissue-specific expression of the transgene in a transformed host plant or a descendant thereof. Preferably, the tissue-specific expression is directed to root tissue or to leaf tissue. More preferably, the tissue-specific expression is directed to root tissue.

In some embodiments, the invention is drawn to a transgenic plant or a transgenic plant cell comprising a recombinant BRRV promoter operably linked to a transgene. In some embodiments, promoter modifications, for example deletions and tandem duplications, provide alternative promoter constructs providing altered transcription patterns. Altered transcription patterns comprise alterations in quantity, timing, and/or tissue specificity in the expression of an operably linked transgene.

The present invention is directed, in some embodiments, to the nucleic acid sequence of the blueberry red ringspot virus and to fragments thereof comprising at least 10 consecutive nucleotides of the full-length sequence. Such fragments provide probes and primers to detect blueberry red ringspot virus DNA in diagnostic tests to ascertain whether a susceptible host plant is infected with the virus.

In some embodiments, the present invention is directed to an isolated nucleic acid molecule comprising a nucleotide sequence capable of hybridizing under stringent conditions to a nucleic acid comprising a sequence of the blueberry red ringspot virus, or a complement thereof.

Among the several advantages achieved by the present invention, therefore, may be noted: the nucleic acid sequence of the blueberry red ringspot virus genome; putative promoters of the blueberry red ringspot virus; a consensus sequence of blueberry red ringspot virus promoters; a vector comprising a recombinant BRRV promoter operably linked to a sequence encoding a polypeptide or an RNA; a transgenic plant or transgenic plant cell comprising a recombinant BRRV promoter operably linked to a sequence encoding a polypeptide or an RNA; a recombinant BRRV promoter that can direct expression of an operably linked DNA sequence encoding a polypeptide or an RNA; a recombinant BRRV promoter that can direct tissue-specific expression of an operably linked DNA sequence encoding a polypeptide or an RNA; a method for transforming a plant or a plant cell with a DNA molecule comprising a recombinant BRRV promoter and an operably linked DNA sequence encoding a polypeptide or an RNA; and a diagnostic method for detecting the presence of blueberry red ringspot virus in a host plant.

BRIEF DESCRIPTION OF THE DRAWINGS

FIG. 1 represents a map (not drawn to scale) of the blueberry red ringspot virus genome.

FIG. 2 represents a comparative alignment of blueberry red ringspot virus putative promoter sequences ‘a’ (nts 221-373 of SEQ ID NO:2) in row one, ‘d’ (nts 235-384 of SEQ ID NO:5) in row two, ‘e’ (nts 131-329 of SEQ ID NO:6) in row three, ‘f’ (nts 205-354 of SEQ ID NO:7) in row four, ‘g’ (nts 257-408 of SEQ ID NO:8) in row five, ‘b’ (nts 176-324 of SEQ ID NO:3) in row six, and ‘c’ (nts 240-389 of SEQ ID NO:4) in row seven, and a consensus DNA sequence for a putative blueberry red ringspot virus promoter derived from the sequence data (SEQ ID NO:10) in row eight.

DETAILED DESCRIPTION OF THE INVENTION

In accordance with the present invention, blueberry red ringspot virus, the pathogen responsible for causing red ringspot disease in blueberry plants, has been sequenced and characterized by standard methods, such as those disclosed in Sambrook, J. C., Fritsch, E. F., and Maniatis, T. (1989) *Molecular Cloning: A Laboratory Manual*, Cold Spring Harbor Laboratory Press, Cold Spring Harbor, N.Y. The virus comprises a circular genome of double stranded DNA. A linearized map of the circular genome (and its putative promoters and open reading frames, discussed below) is shown in FIG. 1, and the sequence in linearized form (SEQ ID NO: 1) is shown in FIG. 2. The virus is sequenced by subcloning restriction fragments into sequencing vectors. Fragments are generated using more than one restriction enzyme, and common sequences are used to order the sequence fragments. Because isolates of the virus from different individual infected plants provide slightly different sequences, a full-length sequence of a BRRV DNA can be different from the sequence disclosed herein. The BRRV sequence comprises at least 8214 base pairs. The nucleic acid sequence of the virus in the present invention (SEQ ID NO: 1) represents a composite assembled from sequences from several isolates and comprises most of the BRRV sequence.

Fragments of the full-length sequence are used as probes and/or as PCR primers to detect the presence of the virus in susceptible host plants according to methods know in the art. Such fragments can be, preferably, at least 10 consecutive nucleotides in length, at least 15 consecutive nucleotides in length, at least 20 consecutive nucleotides in length, at least 50 consecutive nucleotides in length, at least 100 consecutive nucleotides in length or greater up to the full-length viral sequence. Such fragments or complements thereof specifically hybridize to the blueberry red ringspot DNA sequence as shown in FIG. 2, or the complement thereof. Specific hybridization results in hybridization of the fragments or complements thereof to the blueberry red ringspot virus or to a target sequence thereof, preferentially over other DNA molecules that might be present in a sample tested. Hybridization conditions for obtaining such specificity, preferably, involve high stringency conditions as are well know in the art (see Sambrook et al, supra).

Diagnostic methods based upon the probes and/or primers are also within the scope of the present invention. In one diagnostic approach, a nucleic acid sample obtained from a plant suspected of containing the virus is incubated with a nucleic acid probe of the present invention. Incubation conditions are such that the probe will specifically hybridize with any blueberry red ringspot virus nucleic acid that might be present in the sample. Any resultant hybridization complexes formed are then detected using methods well known in the art.

PCR methods are also contemplated in diagnostic methods in which, preferably, two oligonucleotide primers of the present invention serve as a primers for a polymerase chain reaction method. Primers are selected from the sequence as shown in FIG. 2 or the complement thereof, to flank a target sequence which lies within a blueberry red ringspot virus nucleic acid. Any target DNA that might be in a nucleic acid sample obtained from a plant suspected of containing the virus is then amplified by standard methods using the primers. Criteria for selecting primer sequences are well known in the art. The presence of an amplified target DNA sequence is then detected by methods known in the art.

In some embodiments, the present invention includes methods of identifying putative promoters of the blueberry red ringspot virus. In this method, BRRV sequences with the properties of “TATATAA boxes” are identified using computer and/or manual methods (see, e.g., Boyer, T. G., and Maquat, L. E. (1990). Minimal sequence and factor requirements for the initiation of transcription from an atypical TATATAA box-containing housekeeping promoter. *J. Biol. Chem.* 265: 20524-20532). In preferred embodiments, sequence analysis is conducted with the aid of a digital computer programmed with algorithms known in the art, preferably a GCG (University of Wisconsin-Madison) "FIND" software program. In this method, TATATAA-box elements within the BRRV sequence are examined for ATG translational start sites and for classical cis-acting elements, such as AS-1/AS-2-like motifs and GATA boxes. The presence in a sequence of at least one TATATAA-box, at least one classical cis-acting element, and at least one translation start site located 100 base pairs or less downstream from the TATATAA-box provide criteria for designating a BRRV sequence as a putative BRRV promoter.

Analysis of the sequence of the blueberry red ringspot virus by the above method reveals the presence of putative promoters and open reading frames. Seven putative promoters identified using the above criteria are designated "BRRV Promoter A" (SEQ ID NO: 2), "BRRV Promoter B" (SEQ ID NO: 3), "BRRV Promoter C", (SEQ ID NO: 4) "BRRV Promoter D" (SEQ ID NO: 5), "BRRV Promoter E" (SEQ ID NO: 6), "BRRV Promoter F" (SEQ ID NO: 7), and "BRRV Promoter G. (SEQ ID NO: 8)" Their positions in the blueberry red ringspot virus genome are determined by referring to the map in FIG. 1 or the BRRV sequence (SEQ ID NO: 1). In addition, FIG. 1 indicates the relative positions of known open reading frames with respect to the putative promoters. The presence of 7 putative promoters is an unexpected result; another virus within the same family (Caulimoviridae), the cauliflower mosaic virus, is known to comprise only 2 promoters, including at least one which transcribes the entire genome. It is believed that the promoters of the present invention can function as monocotyledonous and dicotyledonous plant cell promoters. However, functional assays of recombinant putative promoter (see below) have revealed promoter activity from only two BRRV promoters.

Open reading frame (ORF) regions are identified as the portion of the sequence extending after the TATA-box element from a start codon to a stop codon. ORF regions are illustrated in FIGS. 1 and 2.

In some embodiments, the promoters of the present invention are incorporated into vectors that can replicate in a host organism. Such vectors are independently-replicating nucleic acid molecules including, for example, plasmids, phages, and viruses. The vectors can be used to transform eukaryotic cells, for example, plant cells, fungi or other eukaryotic cells. Such transformed plant cells include monocotyledonous and dicotyledonous plant cells.

In some embodiments, the invention is a nucleic acid comprising the promoter region operably linked to a sequence encoding a polypeptide or an RNA molecule. Non-limiting examples of a polypeptide include, a fluorescent protein (See, e.g., Chalfie, M., Tu, Y., Euskirchen, G., Ward, W. W., and Prasher, D. C. (1994), Green fluorescent protein as a marker for gene expression. *Science* 263: 802-805); chloramphenicol acetyl transferase; a protein of pharmaceutical interest; and a protein providing a host plant with pest resistance. A non-limiting example of an RNA molecule that can be expressed from a promoter of the present invention is an anti-sense RNA molecule for modulating the expression levels of an endogenous plant gene.

The invention further contemplates methods of demonstrating promoter activity for putative BRRV promoters. In this method, a putative BRRV promoter is operably linked to a reporter gene, for example a DNA encoding a green fluorescent protein or chloramphenicol acetyltransferase. A transgenic plant or plant cell is then generated by transforming the plant or plant cell with the resulting construct. The plant or plant cell, or a descendant thereof comprising the chimeric construct, is then assayed for the presence of the product of the reporter gene. In preferred embodiments, tissues from developing or mature plants are analyzed for the tissue-specific expression. "Tissue-specific expression" is expression of an RNA transcript or a protein product of translation of a transcript, that is at least five times greater than, more preferably at least ten times greater than, and more preferably at least twenty times greater in one tissue compared to another, when measured as a percentage of total RNA synthesis or total polypeptide synthesis in each tissue. One example of a promoter region identified from BRRV is an 821 bp sequence (SEQ ID NO: 9).

In some embodiments, the invention provides a plant or plant cell comprising a recombinant sequence derived from BRRV DNA. Preferably, the plant or plant cell comprises a recombinant sequence derived from BRRV DNA comprising a BRRV promoter sequence. More preferably, the plant or plant cell comprises a recombinant sequence comprising a BRRV promoter sequence operably linked to a nucleic acid encoding a polypeptide or an RNA molecule.

In some embodiments, the invention includes recombinant BRRV promoter constructs comprising multiple copies of a promoter sequence. Tandem repeats of a promoter G sequence or of any of the other promoter sequences can also be made and operably linked to a coding region for a desired expression product such as a reporter gene.

EXAMPLE 1

This example demonstrates isolation, characterization, and sequencing of BRRV DNA.

Blueberry red ringspot virions were isolated from blueberry leaf tissue using the technique of Gillett and Ramsdel (Gillett, J. M., and Ramsdell, D. C. (1984). Detecting the Inclusion forming Blueberry Red Ringspot Virus with ELISA. *Phytopathology* 74: 862). To obtain a sequence of BRRV, viral DNA, obtained from an infected blueberry plant in 1989, was digested with the restriction enzyme Eco RI. Separately, viral DNA obtained from infected blueberry plants at a later date was digested with restriction enzyme Xba I. Fragments digested with either enzyme were ligated into pUC 119 vector digested with either the Eco RI or the Xba I restriction enzyme. Recombinant plasmids were grown and maintained in *E. coli* DH5 alpha cells. Sequences of DNA fragments inserted into the pUC 119 vectors were determined using an ABI automated sequencer and "Big Dye" terminator technology. Once initial sequence was determined, unique primers were designed to "walk" through the sequence of the clone. Sequences obtained from the Xba I and Eco RI digests were then compared, and overlapping sequences were used to determine the relative positions of the fragments in an undigested virus.

EXAMPLE 2

This example demonstrates promoter activity in a recombinant fragment of BRRV sequence.

To demonstrate promoter activity in a fragment of BRRV sequence, an 821 bp fragment (SEQ ID NO: 9) was identified as containing a TATATAA box, at least one cis-acting transcription element, and a translation star the TATATAA box. This fragment was operably linked to a cDNA encoding a green fluorescent protein (GFP). The resulting recombinant construct was used as a transgene to transform plants of the species *Arabidopsis thaliana* using standard procedures. Plant tissues comprising the transgene were assayed for fluorescence indicative of the presence of GFP. All tissues examined exhibited fluorescence, indicating that the sequence of the 821 bp fragment provided promoter activity that was able to direct the expression of the GFP cDNA

EXAMPLE 3

This example demonstrates promoter activity of putative BRRV promoters.

To investigate promoter activity in putative BRRV promoters, a GFP cDNA was operably linked to putative promoters of BRRV identified as above. For comparison, the GFP cDNA was also operably linked to a 35 S promoter of Cauliflower Mosaic Virus (CaMV). *Arabidopsis thaliana* plants were transformed, and transgenic plant tissues, in particular apical meristem, root, and leaf tissue were assayed for the presence of GFP. Relative brightness of fluorescence was estimated by eye using plants transformed with a construct comprising the CaMV 35 S promoter operably linked to GFP cDNA as a standard.

The lengths of putative promoter sequences tested for their ability to support expression of GFP cDNA in *Arabidopsis thaliana* tissue are as follows:

Promoter A—423 nucleotides
Promoter B—429 nucleotides
Promoter C—428 nucleotides
Promoter D—451 nucleotides
Promoter E—401 nucleotides
Promoter F—423 nucleotides
Promoter G—447 nucleotides The results of testing the promoters are presented in Table 1. For promoter G, both truncated sequence fragments as well as tandem duplications of the sequence were also tested for their ability to direct GFP expression. Note that one putative promoter, Promoter A, provides the ability to direct tissue-specific expression of the transgene to the roots.

TABLE 1[a]

| Promoter: | Apical Meristem | Root | Leaf |
|---|---|---|---|
| BRRV G | + | N/A[b] | + |
| BRRV G Short (221 bp) | + | + | (+)[c] |
| BRRV G Shortest (219 bp) | + | − | − |
| BRRV G tandem repeat | N/A[b] | + | + |
| BRRV A | − | ++ | − |
| CaMV 35S | +++ | +++ | + |
| BRRV E | − | + | + |
| BRRV F | − | + | + |

[a] "+++" indicates tissue strongly fluorescent for GFP. "++" indicates tissue exhibiting GFP fluorescence, but less intense than that of comparable tissue from plants transformed with the CaMV 35 S-GFP construct. "+" indicates tissue exhibiting GFP fluorescence, but less intense than that of comparable tissue exhibiting "++" intensity fluorescence. "(−)?" indicates extremely weak, possibly artificial, fluorescence.
[b]N/A not attempted
[c]Fluorescence detectable but weak.

EXAMPLE 3

This example demonstrates discovery and demonstration of a minimal promoter derived from the BRRV DNA sequence.

To isolate a minimal promoter from BRRV, portions of the 821 base pair sequence described above were made. One such fragment, containing only 385 base pairs of DNA, was operably linked to the gene encoding green fluorescent protein, and the resulting construct was used to transform *Arabidopsis thaliana* plants as above. Leaf tissue from these plants exhibited fluorescence indicative of the presence of the green fluorescent protein, thereby demonstrating that a sequence no larger than 385 base pairs comprising promoter G exhibits minimal promoter activity, and can be used to direct expression of heterologous genes in transgenic organisms.

EXAMPLE 4

This example demonstrates the determination of a consensus sequence for a putative minimal promoter.

To determine a consensus sequence for a putative minimal promoter, a computer was used to align the sequences from each of the 7 putative promoters described above. Using standard sequence analysis algorithms, a consensus sequence was derived (SEQ ID NO: 10). This consensus sequence is notable for its high A-T content (approximately 90%).The aligned consensus sequence is shown in FIG. 2 in which consensus bases are shown in capital letters. Dashes represent more than one base as indicated in the possible bases at that position in the seven aligned sequences.

As various changes could be made in the above methods and compositions without departing from the scope of the invention, it is intended that all matter contained in the above description be interpreted as illustrative and not in a limiting sense.

The inventor contemplates that many variations on the disclosed sequences, such as insertions, deletions, inversions, duplications, and substitutions are contemplated as within the scope of this invention. The inventor also contemplates that the promoters and their variants will exhibit distinct expression patterns in terms of both species specificity, tissue specificity and developmental specificity. The inventor also contemplates that sequences hybridizing to the blueberry red ringspot virus under stringent conditions, particularly the putative promoter sequences, will reveal useful activity, in particular promoter activity for use in directing expression of transgenes. It is contemplated that blueberry red ringspot virus nucleic acid sequences having lengths of about 10, 15, 20, 25, or 50 base pairs can be used for hybridization under stringent conditions to isolate new examples of useful sequences having homology to the virus. Sources of DNA for hybridization can be other viruses, plants, animals, fungi, and prokaryotes.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references. As various changes could be made in the above methods and compositions without departing from the scope of the invention, it is intended that all matter contained in the above description be interpreted as illustrative and not in a limiting sense.

What is claimed is:

1. A recombinant nucleic acid, having promoter activity in a plant cell, wherein said nucleic acid comprises the nucleotide sequence of SEQ ID NO:8 or SEQ ID NO:9 or the complement thereof.

2. The recombinant nucleic acid of claim 1 wherein the plant cell is a dicotyledonous plant cell.

3. The recombinant nucleic acid of claim 1 wherein the plant cell is a monocotyledonous plant cell.

4. The recombinant nucleic acid of claim 1, which comprises BRRV promoter region G as set forth in SEQ ID NO:8.

5. The recombinant nucleic acid according to claim 1 operably linked to a DNA sequence encoding a polypeptide or an RNA.

6. A transgenic plant cell comprising the recombinant nucleic acid of claim 5.

7. A transgenic dicotyledonous plant comprising the plant cell of claim 6.

8. A transgenic monocotyledonous plant comprising the plant cell of claim 6.

9. The transgenic plant of claim 6, wherein the plant is of the species *Arabidopsis thaliana*.

10. A method for transforming a plant cell comprising transforming a plant cell with a recombinant DNA construct comprising a blueberry red ringspot virus promoter that comprises the nucleotide sequence of SEQ ID NO:8 or SEQ ID NO:9, or the complement thereof, and a DNA sequence which encodes a polypeptide or an RNA, wherein the promoter regulates the transcription of the DNA sequence.

* * * * *

UNITED STATES PATENT AND TRADEMARK OFFICE
CERTIFICATE OF CORRECTION

PATENT NO. : 7,344,888 B2
APPLICATION NO. : 10/793454
DATED : March 18, 2008
INVENTOR(S) : Richard F. Allison, Jerri Gillett and Christy Mecey It is certified that error appears in the above-identified patent and that said Letters Patent is hereby corrected as shown below:

Column 1, line 60, after "1148", delete ")".

Column 4, line 24, "know" should be --known--.

Column 4, line 38, "know" should be --known--.

Column 4, line 52, after "as", delete "a".

Column 6, line 65, "star" should be --start-- and then insert --sequence less than 100 base pairs from--.

Column 7, line 7, after "cDNA", insert --.--.

Signed and Sealed this

Ninth Day of December, 2008

JON W. DUDAS
*Director of the United States Patent and Trademark Office*

SEQUENCE LISTING

<160> NUMBER OF SEQ ID NOS: 10

<210> SEQ ID NO 1
<211> LENGTH: 8241
<212> TYPE: DNA
<213> ORGANISM: Blueberry Red Ringspot Virus
<220> FEATURE:
<221> NAME/KEY: misc_feature
<222> LOCATION: (7888)..(7888)
<223> OTHER INFORMATION: unknown nucleotide

<400> SEQUENCE: 1

```
ggtatcagag cttgagctac aaatagttca aactcgaaat atcttaatgg aaattcccga      60
tttatcacaa ttatcaaata tagtactcac tgataatcca ggaaccaatc caggaatccc     120
gtataaagga aagattataa gtataccktaa gaatttacta ccagagaaaa ctgagtattc     180
attagcctat gatggatctc atgaacaacg aatattacct atgttaagat ttattactgc     240
tatattaaat aatcaaaccg aaatattaag tttcctatct attaatcaaa taaagtcccg     300
gacagtattc acagaaaaat actttgaaga acaaaagaat aatatatcta tacagcttga     360
acaaaatcgt aaaaatatat tccaaaagtt agaagagcta aaaggattat atgataaaaa     420
acaagatact attatacaac actctaatag gataataaac ctgataaccg aaatagaaca     480
taaaaaagac ttagacgaaa taaaaaatac gctaaaagaa atcaaaaagg atttagtcga     540
aaataataac caaaaagaag ttaaagaatt aatcgaaagt ctaaaagata taagtgatcg     600
aatataaatg actgaaggta acggaaacgg aaaattaacc gaaaaaatag aaaatatgat     660
attaaaatat gaagagttag aaaaagtagt aaaacaagta agtcacgaaa tacatgaaat     720
aaaagaacaa gtagaagtca aaacgacata aaagaattca aggaatcaaa atactataac     780
aacactatcc gagggaatgc ccaacctaca aagaaatga tcatcgataa tcaaccagaa     840
ccatgttatc aaaaagattc accttttcca catctatatc ataccttga tccacaatta     900
aataatataa cagatatgct tatgtatata ataaaaaatt gctgttgcaa agacaagcat     960
gaacagaaag aaaaacaacc tataatacat cctaaaatat tagaagaaaa agaacgacaa    1020
ataaaagatt tagaagatca cataaaagag ttagaagaac acagatgcat aactatttta    1080
gatttaaaga aatattttgg aaataatttt agaggaaaag aggaaagaag accaatagaa    1140
tatctagaag accaacctag ccctagttat agaggaagaa aaccattatg gcctcagata    1200
atatagatca gcaaatcgaa gaaattagaa atatcatgaa taatcttaaa atagaaaaga    1260
ctgaagaaaa tgaaataata tttggaaatg aatcagaaaa tagtgattat gatgtaagaa    1320
tggatgatgt aaaagaagaa ccaggaacta gtaatttcga agaaagatgg aagagaaaaa    1380
gaaatccaac ttacgaatat gaaccatatc ataccgaccc atttattaat gcagaagatt    1440
atggatataa aagaggattc tataaaaata gacaaggtaa atggaaaaaa cctaaagaac    1500
caggtccagt aacaggacga ttagaagatg gaatattaaa tctagattgt ttaactaatg    1560
gagaagaatt attaaaacaa tggacagcaa acaatcatt atcaacacaa attgatgcta    1620
ccatccgaga catggatgct gagaattata caaatatttt aatatataaa acatcaggtg    1680
tagtatttaa ttatatagtt gatatagaca tacctaatat aagctctatg aaaaacctag    1740
aaatattaga ggaaatagct accaaaatat atcaagaatt cctaggagga atgagtaccc    1800
aaagagccac agcggcagat aaacatgatc aagaaagaat aaaatacata ttacataaaa    1860
tgaaaatatg tgacatgtgc gaattcgaag aattctactg tcaatttata cattattatt    1920
```

| | |
|---|---|
| atatgttaga atctaaagag agagctgaat atatgaatgt atttatccag aaactaccag | 1980 |
| aaccccaatt aatacccgac acgttacgag gtatagccaa agtaataaga gcatacatat | 2040 |
| tattacaatg tctaaggaac aagaaaaaat gcaattaatt aatgtaacaa atgttgccca | 2100 |
| aaattcgaat atataccaca taaatttggt tgttcaccaa attcttcttt tcggagggga | 2160 |
| agaaagcgaa ctaaaccaaa tattcaaaat ataaaaacgc aaatatcata cctttaaacc | 2220 |
| atggtataaa aagaaacgat atcgtatgta taaagaaaa tatcaaccca aatataaaca | 2280 |
| aagatattgg aaaaataaaa gtaatcagaa atattgccct aaaggaaaaa aggattgcaa | 2340 |
| gagttggatc tgtcaagaag atggacacta tgcaaatgaa tgccctaaca aagataaaag | 2400 |
| aagagataaa gtaaagctac tagaacaatt atcacaagta aatctcgaac caatagaaaa | 2460 |
| tgataatata tcagaagaag aattatggta tttacaaact gatgaagaat cagaagaaga | 2520 |
| aaatagttca gatgaatcag aacaatactt ttatcaagat aacaatcagt cagaagacga | 2580 |
| tattagcata tattgatcag ggtgcatcat tgtccctata accagaacat aatttaccaa | 2640 |
| aacaattatg gaaagaaaat aagaacccaa ttacaataag agtagccgat aagagagact | 2700 |
| acaattaata aagtagccct tatgattaca atattaatag aaaaaaggaa attccttgta | 2760 |
| cccactatat atcaatttga ttcaggagta ccaatgatta taggaaataa cttttttaaga | 2820 |
| ttatattacc cattttgtca atatctatct tatataacat taagatgtcc taaaatgatc | 2880 |
| aatcaaaaac aagaagtgat taaaataccg atacatcaca gttcacaatt aataaaagca | 2940 |
| aagttactaa acttagtaac aaatattgaa gaacaattat taatgaaaca agttaataaa | 3000 |
| atattacaag aaagattctc actagatttg cttggagaaa agaataaaaa taagaaacta | 3060 |
| atagaaaataa aattaaaaga cccaaatgct gaaatatttg taccaaataa tataccttat | 3120 |
| acccaaagag atatagaaga attcaaagaa gatatggaag atctaataaa caaaggatta | 3180 |
| ataagaccaa gtgaaagtcc acatagtgcg ccagcattct atgtcgaaaa tcattcagaa | 3240 |
| ataaaaagag caaacagaag aattgtaata aattataaag ctatgaatga agccaccatt | 3300 |
| ggaacaccta aaacattacc cagagcagat ttataatgaa cagattagaa cagcacaaag | 3360 |
| gtaaaatttg gttctcaaca ctagatgtaa aatcagccta ctggcaatta agattaactg | 3420 |
| aagaatctaa accattaaca gcatttagtt atccacctca aaaacattac gaatggaatg | 3480 |
| tgttacctat gggattaaag caagctccag gtattttca agaatttatg aatagaagtt | 3540 |
| tacataattt ataacatata tgtttagtat atgttgatga tattattata ttttcagaaa | 3600 |
| aggataaaaa tgatcattta tcaaaagtat tacaagtttt aaaacgatgc gaagatgaag | 3660 |
| gaatcatctt atcacagcca aaagcaaaaa tagcacataa agaaaatgca cataaacaat | 3720 |
| tgatttcttt ggattacata tttcagaagg agaaataata ctacaaccac atattttgga | 3780 |
| aaaattagta ttattccctg atgaaattca gaatcgaaag caattacaaa gatttcttgg | 3840 |
| aaatttaaat tatataagtg aaaaaggatt ttttaaggat tttgcaaaat atcgaaaaga | 3900 |
| tttacaaaag aaagtatcag aaaaagtgcc atggaaatgg acttcctatg acactagtca | 3960 |
| agtgcaagca ctcaaggctt taagccaacg attaccaaga ttatacaatg caaaagaatc | 4020 |
| agacttgctg ataatcgcta ccgatgctag taatggccat tggggagcag ttatgacagc | 4080 |
| agtcactcca gtacatatca ggaattatgg aatatccctt gaggatttat tcccaaaaga | 4140 |
| tcagcataca gcacaagcat tatcatctca atatcagttc ttcggaacaa aggactttgt | 4200 |
| ccaaaaagaa ttacttacta aatatgctag tggaacattc acggataccg aaaaaagata | 4260 |

```
tcctatccat gaattggaaa cattagcagt attacaaact tttcgaaaat ggaaagttga    4320
tttactatca aaacctttta ttttaaaaac agattcaaaa tatgttacag gattttttgag   4380 atataaaata aaagccaatt ataatcaagg acggttgatt agatggcaac ttgaattatc   4440
acaattcaac tataaaactt tttatataaa aggatcagaa aattatggcc ctgacaccct   4500
aaccagggaa tggaaggagc tataaagaca ttggagaatc aaatcagcac taaagagcaa   4560
tcatttcaag caaaaaagca gaagttagca gaactcgaag cagagatcaa caacctcaga   4620
tcaacattag ccatactcag tggagatagc agcaaactat caccatcagc cccagaaaca   4680
acaaagcatt cagtattagc caatattgaa gaagtcaaca acaagtggc agcagccaga    4740 atcaagaagg aatattatgt cattttttaat ggacccatga aggaatcta tgacgaatgg   4800 cataaagcag caccacacat tcaaggacaa tccagcatca ttcacaagaa atatccaacc   4860
attgatgaag caaaaaaggc tcttggagga agctacgcag caatcaccaa cgcaccagca   4920
tcaccaaagg atacaaaagt actattggga agattcaaag tccctttagc accaacgatt   4980
gattcaattc aaactattga gtcaaaaatg aaagcattaa agttactca gaagaaatat    5040 aatgattata tggaaatcgt acacaattac aaggatcaac ataaatcatc acatttctat   5100
ccgaagtacc gagatacaat tggatataaa gcaataatct tgaccgaagc atcagcactc   5160
cccacctatg aattgttcaa aaatggatta gccgacacta tctatttttc ggacataaaa   5220
ccattcaatg attttcctga acgaatcaag caaaccatca acaattattt caagaggttc   5280
gccaaggaaa gaccatgcta catcaaatta ttcagcactc atccaacttt cagtatacaa   5340
ggagaagaag acatgcccag ctatgcagta ctacagatcg gaattagcaa tggagatatg   5400
cctttaatgg acacccttca tatgccagta cccaagcatg aggagttaaa acaaatcaat   5460
ttacagaatt tcattggaat tattaatcat ttatccaatt aacagcaaa cattaaaatg    5520 ctgtataaat ccgatacaat gattatctat tccaaagcca acaaggagat agaaccagat   5580
caagaagaag tattcattca atttgaaaag aattttattg aaaataaaat tccaaaaatg   5640 gcggggggaga tgaagaaaga attatgcaat catatgacca agaagatca tccaggacat    5700 tattgtcaat attgtccatt cattcagcag gatgataagc agtcagcatc aagtgaagaa   5760
gaaaagatca ccatggaagt ggaggaataa aacgtcttca tccatcacta tcaagatgta   5820
gacattacaa tgtaaagcta cggctattat taggcttaga atctacgcca atgtaaagta   5880
gattccctta tcttttattt tgtaagtttg aagtccggat ctgagttacg cctgtgagaa   5940
ttcctgtata taaggacgac ctatcctatg tttgtagtca gagtgttttc catatgtcga   6000
ataaacgtct aacgtttga aggtgtcgcc ctttcactct ccaatgttga gttcttcgta    6060
tgaagatatc tgaagagcac atcctatccc tatatacct atccttaacc tatcccaaat    6120
tctatcccaa aggttttgtt gcagaagcaa aactttcatg gattcaagac aggattcctc   6180
gaagaacaag tatatgccta aactaccact attttatctc tatctgtgtg tacttattca   6240
tttcattata tcgattttgt tattactctt tcttgttatc atgatatgtc aaatcaaact   6300
actttgttga acaattatta tctacagtct tatattattg gaattataaa tgaagaata    6360 agattaatat tagattgaca caggagcagc tatgtccttt ataaaacaat gatctcgttc   6420
atcaataatc attaacacct attcaacctt atacagtaaa aggatattta gatcatcata   6480
caattggaga caaatactta gtagaacatt ctaccaaaca taaatgtcat attaagtaac   6540
acctttaaca aaacattatt actaaaaaca actcaaacaa aagcagatgt attaggagcc   6600
gaagtattat tcggaatgga tttttttagat agctttgaat catattcaat cacaaaggaa  6660
```

```
caactaatac taagagaagg aaatattact cattatatac caagaatcac agtcgataca    6720
gacaccataa gagaaaccct aaactattaa agatgtcatc acctattata ttagaccaag    6780
caggagtagt ccaaaatcaa gaacagaatc aaatatcaaa agttagtaat caaaatcaga    6840
tgtcaagaat agaagatcaa aaccaatctg aagaaatcag acatatcaat caaatctttg    6900
atattataca atcaaatgaa acaaatgatt attatggagt cgatgtccaa ctagaaagat    6960
ctaaactaaa acaaatagca aagaaggaa aattaacatt aaaatcagga caaggaataa      7020
aatcagaagg attcttacca tctattacta gaaagaatat attatatcta ggaaaattta    7080
caagcgaaca accattagaa ataagcacag cagtaggaca agaagcacta tcattagtta    7140
atggaaagca gatagcagac cgaatagcta aaatgaaaca atcagataaa gaaaaaattc    7200
agtatataca tataagcaca atacaaatac tagttaagtc tacttatgcc tcaatagata    7260
cacccatgga tattatagtt attgataata gaataatttc taaaaataag aaagaacaag    7320
ttctaggaat aattaaagga aatctgaaat atggagttat taagtttgat gtaagtttac    7380
acttcgctat accattagta actaagaact taagtcaatc aataggaata ttatataagt    7440
tccacagaca ggatctgatg gaaaaaggag attacccact tagtattacc tactctgtag    7500
gatatgcatt aagcaatagc caccatagtg ttgattatat agatcaagag attatacata    7560
tagacgattt atttaaaaat actagtacta aattagtaac atttgagaaa aagaatgaaa    7620
acgccaacga catatttaga gcaccaccag taagaatgat taaaccaaga gaggatttat    7680
caaaaccaac tataacagat gtcacagacc cattaaaacc aaccaccagt agttctatcc    7740
aattagcacc tccacctaac ctacatagaa accagagag catgcagaac ttagaaaagc      7800
aaatacagga attaagaaga acagttacaa acctcaatga caaaatatga gctatcagta    7860
tagaagagga ccatatatga aaggaagnta taaacgatgt ctcatagaag atttagaacc    7920
catgaaggac atactagtaa ctactaagag agaaatatta gaacaatttt ccagatctga    7980
agaaagatca aaaataatta gcaatttgca aggattaatt gattatttag tcaaaagaca    8040
gaaacgagaa gcagaaaatc cggaattaac catccaagaa aagatattaa cgagattgaa    8100
cagcattgaa gaaaaattag agaagtctaa ttcattttca tcaatatttg atgatctaga    8160
agaaacttct caccaaacaa atcaggtcaa tattccgcca tctagtgaaa actagtaagt    8220
tgaccgcccc ggtccgtttt t                                              8241
```

<210> SEQ ID NO 2
<211> LENGTH: 423
<212> TYPE: DNA
<213> ORGANISM: Blueberry Red Ringspot Virus

<400> SEQUENCE: 2

```
gttaaagaat taatcgaaag tctaaaagat ataagtgatc gaatataaat gaccgaaggt      60
accggaaatg gaaaattaac cgaaaaaata gaaaatatga tattaaaata tgaagagtta    120 gaaaagtag taaacaagt aagtcacgaa atacatgaaa taaagaaca agtgaagtc         180 gaaagcgaca taaagaatt taaggaatca aaatactata acaacactat ccgagggaat    240
gcccaaccta caaagaaat gatcatcgat aatcaaccag aacctgtta tcaaaaagat      300 tcaccttttc cacatctata tcatacctttt gatccacaat taaataatat aacagatatg    360
cttatgtata taataaaaaa ttgctgttgc aaagacaagc atgaacagaa agaaaaacaa    420
cct                                                                  423
```

```
<210> SEQ ID NO 3
<211> LENGTH: 429
<212> TYPE: DNA
<213> ORGANISM: Blueberry Red Ringspot Virus

<400> SEQUENCE: 3
tgtaaaagaa gaaccaggaa ctagtaattt cgaagaaaga tggaagagat aaagcaatcc      60
aacttatgaa tatgaaccat atcataccga cccatttatt aatgcagaag attatggata    120
taaaggagga ttctataaaa atagacaagg taaatggaaa aaacctaaag aaccaggtcc    180
agtaacagga cgattagaag atggaatatt aaatctagat tgtttaacta atggagaaga    240
attattaaaa caatggacag caaaacaatc attatcaaca caaattgatg ctaccatccg    300
agacatggat gctgagaatt ataacaagta tttaatatat aaaacatcag gtgtagtatt    360
taattatata gttgatatag acatacctaa tataagctct atgaaaaacc tagaaatatt    420
agaggaaat                                                             429

<210> SEQ ID NO 4
<211> LENGTH: 428
<212> TYPE: DNA
<213> ORGANISM: Blueberry Red Ringspot Virus

<400> SEQUENCE: 4
tatcagaaga agaattatgg tatttacaaa ctgatgaaga atcagaagaa gaaaatagtt      60
cagatgaatc agaacaatac ttttatcaag ataacaatca gtcagaagac gatattagca    120
tatattgatc agggtgcatc attgtcccta taaccagaac ataatttacc aaaacaatta    180
tggaaagaaa ataagaaccc aattacaata agagtagccg ataagagaga ctacaattaa    240
taaagtagcc cttatgatta caatattaat agaaaaaagg aaattccttg tacccactat    300
atatcaattt gattcaggag taccaatgat tataggaaat aacttttaa gattatatta    360
cccatttgt caatatctat cttatataac attaagatgt cctaaaatga tcaatcaaaa    420
acaagaag                                                              428

<210> SEQ ID NO 5
<211> LENGTH: 451
<212> TYPE: DNA
<213> ORGANISM: Blueberry Red Ringspot Virus

<400> SEQUENCE: 5
ttaaaatacc aatacatcac agttcacaat taataaaagc aaagttacta aacttagtaa      60
caaatattga agaacaatta ttaatggaac aagttaataa aatattacaa gaaagattct    120
cactagattt gctaggagaa aagaataaaa ataaagaact aatagaaata aaattaaaa    180
gacccaaatg ctgaaatatt tgtaccaaat aatataccttt atacccaaag agatatagaa    240
aaagtccaca tagtgcgcca gcattctatg tagaaaatca ttcagaaata aaagagcat    300
taagaagaat tgttataaat tataaagcta ttgaatgaag ccaccattgg aacacctaaa    360
cattacccag agcagattat ataatgaaca gattaaaagg aaaaatatgg ttttcaacac    420
tagatgtaaa atcagcctac tggcaattaa g                                    451

<210> SEQ ID NO 6
<211> LENGTH: 401
<212> TYPE: DNA
<213> ORGANISM: Blueberry Red Ringspot Virus

<400> SEQUENCE: 6
```

```
tttttcaaga atttatgaat agaagtttac ataatttaga acatatatgt ttagtatatg      60
ttgatgatat tattatattt tcagaaaagg ataaaaatga tcatttatca aaagtattac     120
aagttttaaa acgatgcgaa gatgaaggaa tcatcttatc acagccaaaa gcaaaaatag     180
cacataaaga aattgatttc tttggattca tatttcagaa ggagaaataa tactacaacc     240
acatattttt ggaaaaatta gtattattcc ctgatgaatt cagaatcgaa agcaattaca     300
aagatttctt ggaaatttaa attatataag tgaaaaagga ttttttaagg attttgcaaa     360
atatcgaaaa gatttacaaa agaaagtatc agaaaaagtg c                         401

<210> SEQ ID NO 7
<211> LENGTH: 423
<212> TYPE: DNA
<213> ORGANISM: Blueberry Red Ringspot Virus

<400> SEQUENCE: 7
cccttgagga tttattccca aaagatcagc atacagcaca agcattatca tctcaatatc      60
agttcttcgg aacaaaggac tttgtccaaa aagaattact tactaaatat gctagtggaa     120
cattcacgga taccgaaaaa agatatccta tccatgaatt ggaaacatta gcagtattac     180
aaacttttcg aaaatggaaa gttgattac tatcaaaacc tttttatttta aaaacagatt     240 caaaatatgt tacaggattt tgagatata aaataaaagc caattataat caaggacggt     300
tgactagatg gcaacttgaa ttatcacaat tcaactatag aacttttttat ataaaaggat     360 cagaaaatta tggccctgac accctaacca gggaatggaa ggagctataa agacattgga     420
gaa                                                                   423

<210> SEQ ID NO 8
<211> LENGTH: 447
<212> TYPE: DNA
<213> ORGANISM: Blueberry Red Ringspot Virus

<400> SEQUENCE: 8
tttttaccat ctattactag aaagaatata ttatatttag gaaagttcac cagcgagcaa      60
ccattagaaa ttagcacagc agtaggacaa gaagccttat cattagttaa tggaaagcaa     120
atagcagaca gaataacaaa aatgaaacaa tcagataaag aaaagattca gtatatacac     180
ttaagcacaa tacagatatt agttaaatcc acctatgcct caatagatac accaatggat     240
attatagttg ttgataatag aataatttct aaaaataaga agaacaagt tctaggaata     300 attaaaggaa atctgaaata tggagtatta agttcgacgt aagtttacac ttcgccatac     360
cattagtaac taagaatttta agccaatcta taggaatatt atataaattc cacagacaag     420
atctgatgga aaaggagat tacccac                                          447

<210> SEQ ID NO 9
<211> LENGTH: 821
<212> TYPE: DNA
<213> ORGANISM: Blueberry Red Ringspot Virus

<400> SEQUENCE: 9
ataccaagaa tcacggtaga tacagaaact ataagagaaa ctttgaatta ttaagatgtc      60
atcacctatc atattagatc aagcaggagt aatccaaaat caagaacaaa atcaagaaca     120
gaatcaaatg tcaagagtca ataatcgaa tcagatgtca aaatagaag atcagaatca     180 atcagaagaa atcagacata ttaatcaaat ctttgatatt atccaatcaa atgaaacaaa     240
```

```
tgattattat ggagtcgatg tccaactaga aagatctaaa ctaaaacaaa tagcaaagaa      300
ggaaaattaa cattaaaatc tggacaagga ataaaatcag aaggattttt accatctatt      360
actagaaaga atatattata tttaggaaag ttcaccagcg agcaaccatt agaaattagc      420
acagcagtag gacaagaagc cttatcatta gttaatggaa agcaaatagc agacagaata      480
acaaaaatga aacaatcaga taaagaaaag attcagtata tacacttaag cacaatacag      540
atattagtta aatccaccta tgcctcaata gatacaccaa tggatattat agttgttgat      600
aatagaataa tttctaaaaa taagaaagaa caagttctag gaataattaa aggaaatctg      660
aaatatggag tattaagttc gacgtaagtt tacacttcgc cataccatta gtaactaaga      720
atttaagcca atctatagga atattatata aattccacag acaagatctg atggaaaaag      780
gagattaccc acttagtatc acctactcag taggatatgc a                         821
```

```
<210> SEQ ID NO 10
<211> LENGTH: 151
<212> TYPE: DNA
<213> ORGANISM: Blueberry Red Ringspot Virus
<220> FEATURE:
<221> NAME/KEY: misc_feature
<222> LOCATION: (6)..(6)
<223> OTHER INFORMATION: a or g or c or t, unknown, or other
<220> FEATURE:
<221> NAME/KEY: misc_feature
<222> LOCATION: (143)..(143)
<223> OTHER INFORMATION: a or g or c or t, unknown, or other
<220> FEATURE:
<221> NAME/KEY: misc_feature
<222> LOCATION: (142)..(142)
<223> OTHER INFORMATION: a or g or c or t, unknown, or other
<220> FEATURE:
<221> NAME/KEY: misc_feature
<222> LOCATION: (139)..(139)
<223> OTHER INFORMATION: a or g or c or t, unknown, or other
<220> FEATURE:
<221> NAME/KEY: misc_feature
<222> LOCATION: (136)..(136)
<223> OTHER INFORMATION: a or g or c or t, unknown, or other
<220> FEATURE:
<221> NAME/KEY: misc_feature
<222> LOCATION: (132)..(132)
<223> OTHER INFORMATION: a or g or c or t, unknown, or other
<220> FEATURE:
<221> NAME/KEY: misc_feature
<222> LOCATION: (124)..(124)
<223> OTHER INFORMATION: a or g or c or t, unknown, or other
<220> FEATURE:
<221> NAME/KEY: misc_feature
<222> LOCATION: (113)..(113)
<223> OTHER INFORMATION: a or g or c or t, unknown, or other
<220> FEATURE:
<221> NAME/KEY: misc_feature
<222> LOCATION: (108)..(108)
<223> OTHER INFORMATION: a or g or c or t, unknown, or other
<220> FEATURE:
<221> NAME/KEY: misc_feature
<222> LOCATION: (107)..(107)
<223> OTHER INFORMATION: a or g or c or t, unknown, or other
<220> FEATURE:
<221> NAME/KEY: misc_feature
<222> LOCATION: (95)..(95)
<223> OTHER INFORMATION: a or g or c or t, unknown, or other
<220> FEATURE:
<221> NAME/KEY: misc_feature
<222> LOCATION: (91)..(91)
<223> OTHER INFORMATION: a or g or c or t, unknown, or other
<220> FEATURE:
<221> NAME/KEY: misc_feature
<222> LOCATION: (83)..(83)
<223> OTHER INFORMATION: a or g or c or t, unknown, or other
<220> FEATURE:
<221> NAME/KEY: misc_feature
```

```
<222> LOCATION: (68)..(68)
<223> OTHER INFORMATION: a or g or c or t, unknown, or other
<220> FEATURE:
<221> NAME/KEY: misc_feature
<222> LOCATION: (52)..(52)
<223> OTHER INFORMATION: a or g or c or t, unknown, or other
<220> FEATURE:
<221> NAME/KEY: misc_feature
<222> LOCATION: (40)..(40)
<223> OTHER INFORMATION: a or g or c or t, unknown, or other
<220> FEATURE:
<221> NAME/KEY: misc_feature
<222> LOCATION: (37)..(37)
<223> OTHER INFORMATION: a or g or c or t, unknown, or other
<220> FEATURE:
<221> NAME/KEY: misc_feature
<222> LOCATION: (30)..(30)
<223> OTHER INFORMATION: a or g or c or t, unknown, or other
<220> FEATURE:
<221> NAME/KEY: misc_feature
<222> LOCATION: (27)..(27)
<223> OTHER INFORMATION: a or g or c or t, unknown, or other
<220> FEATURE:
<221> NAME/KEY: misc_feature
<222> LOCATION: (16)..(16)
<223> OTHER INFORMATION: a or g or c or t, unknown, or other
<220> FEATURE:
<221> NAME/KEY: misc_feature
<222> LOCATION: (6)..(6)
<223> OTHER INFORMATION: a or g or c or t, unknown, or other
<220> FEATURE:
<221> NAME/KEY: misc_feature
<222> LOCATION: (2)..(2)
<223> OTHER INFORMATION: a or g or c or t, unknown, or other

<400> SEQUENCE: 10
anacantatc caatangttt acaagantan aaaatanaan atcattgata anataaaaga      60 gatataaat taaacaatt aanattaaaa ncatntgaat taagccnnaa atntaataac      120
aaanaattta tnaaanttna tnntatataa a                                   151
```